United States Patent
Martens et al.

(10) Patent No.: US 12,345,676 B2
(45) Date of Patent: Jul. 1, 2025

(54) FIELD-EFFECT TRANSISTOR-BASED BIOSENSOR

(71) Applicant: IMEC VZW, Leuven (BE)

(72) Inventors: Koen Martens, Ghent (BE); Karolien Jans, Tessenderlo (BE); Pol Van Dorpe, Spalbeek (BE); Gabrielle Woronoff, Brussels (BE)

(73) Assignee: Imec VZW, Leuven (BE)

( * ) Notice: Subject to any disclaimer, the term of this patent is extended or adjusted under 35 U.S.C. 154(b) by 486 days.

(21) Appl. No.: 16/673,342

(22) Filed: Nov. 4, 2019

(65) Prior Publication Data

US 2020/0141898 A1    May 7, 2020

(30) Foreign Application Priority Data

Nov. 5, 2018 (EP) .................................. 18204356

(51) Int. Cl.
*G01N 27/414* (2006.01)
*B01L 3/00* (2006.01)
*C12Q 1/00* (2006.01)

(52) U.S. Cl.
CPC .......... *G01N 27/4145* (2013.01); *B01L 3/502* (2013.01); *C12Q 1/005* (2013.01);
(Continued)

(58) Field of Classification Search
CPC .. G01N 27/4145; G01N 27/414; G01N 33/50; G01N 33/53; G01N 33/543;
(Continued)

(56) References Cited

U.S. PATENT DOCUMENTS

| 5,356,757 A * | 10/1994 | Shionoya ............... C12Q 1/003 |
| | | 430/315 |
| 9,018,740 B2 * | 4/2015 | Charrier ............... G01N 27/414 |
| | | 257/E39.007 |

(Continued)

FOREIGN PATENT DOCUMENTS

KR      20100044975    * 10/2008

OTHER PUBLICATIONS

Marrakchi et al., "Development of trypsin biosensor based on ion sensitive field-effect transistors for proteins determination", 2006, Materials Science and Engineering: C, vol. 26, p. 369-373 (Year: 2006).*

(Continued)

*Primary Examiner* — Ann Montgomery
*Assistant Examiner* — Chau N. B. Tran
(74) *Attorney, Agent, or Firm* — McDonnell Boehnen Hulbert & Berghoff LLP (57) ABSTRACT

A sensor is provided. The sensor includes a field effect transistor comprising: an active region comprising a source region, a drain region, and a channel region between the source region and the drain region; a dielectric region on the channel region; an enzyme coupled to the dielectric region, the enzyme having an active site for interacting with a substrate; an electrolyte-screening layer coupled to the dielectric region, covering part of the enzyme while leaving the active site uncovered, thereby permitting interaction of the substrate with the active site, and a fluidic gate region to which the active site of the enzyme is exposed. A biosensing device including one or more of the sensors is also provided.

20 Claims, 4 Drawing Sheets

(52) U.S. Cl.
CPC ... *B01L 2300/0636* (2013.01); *B01L 2300/12* (2013.01); *B01L 2400/0415* (2013.01)

(58) Field of Classification Search
CPC ..... G01N 33/54366; G01N 33/543673; G01N 33/5438; B01L 3/502; B01L 2300/0636; B01L 2300/12; B01L 2400/0415; C12Q 1/005
See application file for complete search history.

(56) References Cited

U.S. PATENT DOCUMENTS

| | | | | |
|---|---|---|---|---|
| 2005/0250097 | A1* | 11/2005 | Duffy | B82Y 5/00 435/15 |
| 2005/0255514 | A1* | 11/2005 | De Palma | G01N 33/552 435/6.12 |
| 2006/0269915 | A1* | 11/2006 | Yukimasa | C12Q 1/42 435/6.12 |
| 2007/0132043 | A1* | 6/2007 | Bradley | G01N 27/4146 257/414 |
| 2019/0360039 | A1* | 11/2019 | Bashkirov | B01L 3/502761 |

OTHER PUBLICATIONS

Gül et al., "Single Molecule Bioelectronics and Their Application to Amplification-Free Measurement of DNA Lengths", 2016, Biosensors (Basel), vol. 6, p. 1-19 (Year: 2016).*

Bhardwaj, "A Review on Immobilization Techniques of Biosensors", 2014, International Journal of Engineering Research & Technology, vol. 3 issue 5, 5 pages (Year: 2014).*

Mentlein, "Cell-Surface Peptidases", 2004, International Review of Cytology, vol. 35, 49 pages (Year: 2004).*

Kalra et al. (Schottky Barrier FET Biosensor for Dual Polarity Detection: A Simulation Study, IEEE Electron Device Letters, vol. 38, No. 11, Nov. 2017) (Year: 2017).*

Boutureira, O., et al., "Advances in Chemical Protein Modification", Chemical Reviews, Feb. 20, 2015, vol. 115, pp. 2174-2195, doi.10.1021/cr500399p.

Chan, A.O-Y., et al., "Modification of N-Terminal α-Amino Groups of Peptides and Proteins Using Ketenes", Journal of the American Chemical Society, Jan. 30, 2012, vol. 134, pp. 2589-2598, doi:10.1021/ja208009r.

Chen, D., et al., "Selective N-terminal Functionalization of Native Peptides and Proteins", Chemical Science, Jan. 9, 2017, vol. 8, pp. 2717-2722, doi:10.1039/c6sc04744k.

Elsohly, A.M., et al., "Development of Oxidative Coupling Strategies for Site-Selective Protein Modification", Accounts of Chemical Research, Jun. 9, 2015, vol. 48, pp. 1971-1978, doi:10.1021/acs.accounts.5b00139.

Granéli, A., et al., "Formation of Supported Lipid Bilayer Membranes on SiO2 from Proteoliposomes Containing Transmembrane Proteins", Langmuir, 2003, vol. 19(3), pp. 842-850.

Gilmore, J.M., et al. "N-Terminal Protein Modification through a Biomimetic Transamination Reaction", Angew. Chem. Int. Ed., 2006, vol. 45, pp. 5307-5311, doi:10.1002/anie.200600368.

Humenik, M., et al., "C-Terminal Incorporation of Bio-Orthogonal Azide Groups into a Protein and Preparation of Protein-Oligodeoxynucleotide Conjugates by Cu1-Catalyzed Cycloaddition", ChemBioChem, 2007, vol. 8, pp. 1103-1106, doi:10.1002/cbic.200700070.

Keller, C.A., et al., "Formation of Supported Membranes from Vesicles", Physical Review Letters, Jun. 5, 2000, vol. 84(23), pp. 5443-5446.

Reimhult, E., et al., "Intact Vesicle Adsorption and Supported Biomembrane Formation from Vesicles in Solution: Influence of Surface Chemistry, Vesicle Size, Temperature, and Osmotic Pressure", Langmuir, 2003, vol. 19(5), pp. 1681-1691, doi:10.1021/la0263920.

Rosen, C.B., et al., "Targeting the N-terminus for Site-Selective Protein Modification", Nature Chemical Biology, Jun. 20, 2017, vol. 13, pp. 697-705, doi:10.1038/nchembio.2416.

Sasaki, T., et al., "N-Terminal Labeling of Proteins by the Pictet-Spengler Reaction", Bioorganic & Medicinal Chemistry Letters, Jul. 15, 2008, vol. 18, pp. 4550-4553, doi:10.1016/j.bmcl.2008.07.033.

Song, I.T., et al., "PEGylation and HAylation via Catechol: α-Amine-Specific Reaction at N-terminus of Peptides and Proteins", Acta Biomaterialia, Jul. 14, 2016, vol. 43, pp. 50-60, doi:10.1016/j.actbio.2016.07.018.

Temming, R.P., et al., "N-terminal Dual Protein Functionalization by Strain-Promoted Alkyne-Nitrone Cycloaddition", Organic & Biomolecular Chemistry, Feb. 20, 2013, vol. 11, pp. 2772-2779, doi:10.1039/c3ob00043e.

Choi, Yongki et al., "Single-Molecule Lysozyme Dynamics Monitored by an Electronic Circuit", Science, vol. 335, Jan. 20, 2012, pp. 319-324.

Olsen, Tivoli J. et al., Electronic Measurements of Single-Molecule Processing by DNA Polymerase I (Klenow Fragment), Journal of the American Chemical Society, vol. 135, 2013, 18 pages.

Sims, Patrick C. et al., "Electronic Measurements of Single-Molecule Catalysis by cAMP-Dependent Protein Kinase A", Journal of the American Chemical Society, vol. 135, 2013, pp. 7861-7868.

* cited by examiner

FIELD-EFFECT TRANSISTOR-BASED BIOSENSOR

CROSS-REFERENCE TO RELATED APPLICATIONS

The present application is a non-provisional patent application claiming priority to European Patent Application No. EP18204356.2, filed Nov. 5, 2018, the contents of which are hereby incorporated by reference.

TECHNICAL FIELD OF THE DISCLOSURE

The present disclosure relates to the field of Field-Effect Transistor-based biosensors and to their fabrication.

BACKGROUND OF THE DISCLOSURE

Biosensors based on the detection of a single molecule by an enzyme have been described. These devices are important as they can potentially be adapted to allow massive parallel bio-sensing. Applications where such devices are of interest are for instance protein analysis, proteomics (massively parallel protein identification or fingerprinting), immunoassays (antibody or antigen monitoring), and DNA sequencing, amongst others.

Biosensors based on the detection of a single molecule by an enzyme are currently making use of fluorescence and optical detection. This technology imposes limits on the potential sensor density and hence data throughput due the wave properties of light and the maximum possible pixel density of optical sensors. Electrical single molecule sensing of enzyme or protein activity making use of field effect devices (ISFETs, Ion Sensitive Field Effect Transistors) has currently only been reported in a handful of papers which make use of carbon nanotube FETs [Choi et al. Science (2012), Vol. 335, pp. 319-324; Sims et al. J. Amer. Chem. Soc. (2013), Vol. 135, pp. 7861-7868; and Olsen et al. J. Amer. Chem. Soc. (2013), Vol. 135, pp. 7855-7860]. Due to their very small diameter, carbon nanotubes allow the manufacture of highly sensitive sensors. Unfortunately, carbon nanotube FETs are currently not deemed a mass-manufacturable technology.

Biosensors based on more traditional semiconductors, such as silicon, would have the advantage of being mass-manufacturable, but they typically suffer from a low sensitivity.

There is, therefore, a need in the art for new biosensors having a good sensitivity.

SUMMARY OF THE DISCLOSURE

It is an object of the present disclosure to provide FET-based sensors and biosensing devices comprising the same.

Some embodiments of the present disclosure may provide FET-based sensors that have a good sensitivity. This is obtained by reducing the screening effect operated by the electrolyte on the target molecule. In embodiments, this can be done while keeping the screening effect operated by the electrolyte on the non-target molecules.

Various embodiments of the present disclosure may provide FET-based sensors that can be mass-produced.

Some embodiments of the present disclosure may provide FET-based sensors that can be produced at low cost.

Various example embodiments of the present disclosure may provide a high integration density.

In a first aspect, the present disclosure relates to a sensor. The sensor comprises a field effect transistor (FET). The FET comprises:
   an active region comprising a source region, a drain region, and a channel region between the source region and the drain region;
   a dielectric region on the channel region;
   an enzyme coupled to the dielectric region, the enzyme having an active site for interacting with a substrate;
   an electrolyte-screening layer coupled to the dielectric region, covering at least part of the enzyme while leaving the active site uncovered, thereby permitting interaction of the substrate with the active site; and
   a fluidic gate region to which the active site of the enzyme is exposed.

In a second aspect, the present disclosure relates to a biosensing device comprising a sensor according to any embodiment of the first aspect.

In a third aspect, the present disclosure relates to a method for manufacturing a sensor. The method comprises forming a field effect transistor (FET). Forming the FET comprises:
   providing an active region comprising a source region, a drain region, and a channel region between the source region and the drain region;
   providing a dielectric region on the channel region;
   coupling an enzyme to the dielectric region, the enzyme having an active site for interacting with a substrate;
   coupling an electrolyte-screening layer to the dielectric region so that the electrolyte-screening layer covers at least part of the enzyme while leaving the active site uncovered, thereby permitting interaction of the substrate with the active site; and
   forming a fluidic gate region to which the active site of the enzyme is exposed.

It has been determined that biosensors comprising an FET (bioFET), and especially silicon-based such biosensors, suffer from a low sensitivity due to electrolyte screening. Indeed, the presence of an electrolyte between the target molecule and the channel of the FET severely weakens the electric field generated by the target molecule. This problem could be solved by detecting the target molecule in a solution of low salinity, however, for convenience, one would like to operate the bioFET at the relatively high physiological salinity level of typical biological samples. Working at the salinity level of typical biological samples also has the advantage of reducing non-specific binding to the bioFET surface.

The above objective can be accomplished by a sensor and a biosensing device having an electrolyte screening layer reducing the electrolyte thickness present between the channel of the FET and the target molecule.

The above objective can be accomplished by a method and device according to the present disclosure.

Particular aspects of the disclosure are set out in the accompanying independent and dependent claims. Features from the dependent claims may be combined with features of the independent claims and with features of other dependent claims as appropriate and not merely as explicitly set out in the claims.

Although there has been constant improvement, change, and evolution of devices in this field, the present concepts are believed to represent substantial new and novel improvements, including departures from prior practices, resulting in the provision of more efficient, stable, and reliable devices of this nature.

The above and other characteristics, features, and advantages of the present disclosure will become apparent from the following detailed description, taken in conjunction with the accompanying drawings, which illustrate, by way of example, the principles of the disclosure. This description is given for the sake of example only, without limiting the scope of the disclosure. The reference figures quoted below refer to the attached drawings.

BRIEF DESCRIPTION OF THE DRAWINGS

FIG. 2 is analogous to FIG. 1 but the electrolyte-screening layer 7 is a lipid bilayer 11. FIG. 2 also depicts the fluidic gate region 8.

FIG. 3 is analogous to FIG. 2 but a lipid monolayer 9 is used between the binding layer and the enzyme to provide a good barrier against the electrolyte.

FIG. 4 is analogous to FIG. 2, but the lipid bilayer is replaced by a lipid monolayer 9.

FIG. 5 is a representative schematic illustration of vertical cross-sections of sensors, illustrating an aspect of the present disclosure. In an embodiment shown on the left, a bonded substrate 6 is shown which is not enveloped by the enzyme 4 and hence strongly screened from the channel by the surrounding electrolyte 10. In the two illustrations further to the right, the enzyme is selected in such a way that the active site 5 envelops the substrate to some degree and thereby expels the electrolyte present between the substrate and the enzyme body. The choice of the enzyme and its orientation on the FET dielectric region 2 are such that screening of the substrate charge by the electrolyte 10 is prevented to a significant extent. Different depths of enveloping binding pockets are illustrated. The envelopment allows reducing screening by the electrolyte.

In the different figures, the same reference signs refer to the same or analogous elements.

DESCRIPTION OF ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. The term "comprising" therefore covers the situation where only the stated features are present and the situation where these features and one or more other features are present. Thus, the scope of the expression "a device comprising means A and B" should not be interpreted as being limited to devices consisting only of components A and B. It means that with respect to the present disclosure, the only relevant components of the device are A and B.

Similarly, it is to be noticed that the term "coupled", also used in the claims, should not be interpreted as being restricted to direct connections only. The terms "coupled" and "connected", along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various aspects. This method of disclosure, however, is not to be interpreted as reflecting an intention that the claimed disclosure requires more features than are expressly recited in each claim. Rather, as the following claims reflect, aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the disclosure.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

The disclosure will now be described by a detailed description of several embodiments of the disclosure. It is clear that other embodiments of the disclosure can be configured according to the knowledge of persons skilled in the art without departing from the technical teaching of the disclosure, the disclosure being limited only by the terms of the appended claims.

The first aspect of the present disclosure relates to a sensor.

The sensor may be for sensing a target molecule. Typically, the sensor may be for sensing a single target molecule at a time. The target molecule may be a substrate of an enzyme, i.e. a biomolecule. The target molecule may be typically charged. The presence of this charge close to the channel can be felt by the FET. The target molecule may be in a liquid medium, typically an electrolyte. Most typically, the liquid medium may be an aqueous electrolyte medium such as a biological fluid. The device of the present disclosure can be particularly well suited to detect the target molecule in a biological fluid. Prior to the present disclosure, the detection of a target molecule in a biological fluid with a BioFET was problematic due to the high salinity, and therefore the high screening effect of typical biological samples. This problem is addressed by the present disclosure.

The sensor of the present disclosure may be typically referred to as a BioFET. BioFETs sense molecules as charges or dielectric displacements close to their gate dielectric. These transistors do not have their solid gate electrode directly in contact with the gate dielectric. Instead, they have a liquid electrolyte gate in contact with the gate dielectric and the solid gate electrode is in electrical contact with the liquid electrolyte gate. The sensed molecules can be located in this liquid gate near the gate dielectric surface. The molecular charge or dielectric displacement near the gate dielectric can cause a change in the current running through the semiconductor channel of the device as dictated by the disturbance in the electrical potential landscape these molecules cause.

The sensor comprises a field effect transistor (FET).

The FET comprises:
- an active region comprising a source region, a drain region, and a channel region between the source region and the drain region;
- a dielectric region on the channel region;
- an enzyme coupled to the dielectric region, the enzyme having an active site for interacting with a substrate;
- an electrolyte-screening layer coupled to the dielectric region, covering at least part of the enzyme while leaving the active site uncovered, thereby permitting interaction of the substrate with the active site; and
- a fluidic gate region to which the active site of the enzyme is exposed.

The active region typically comprises a semiconductor material such as, but not limited to, silicon.

The active region comprises a channel region. In embodiments, the channel region may have a length in a range from 10 to 150 nm. In embodiments, the channel region may have a width in a range from 3 to 20 nm. In embodiments, the channel region may have a height in a range from 5 to 40 nm.

The dielectric region typically comprises a dielectric material, such as for instance a silicon oxide (e.g. $SiO_2$) or a high-k dielectric (e.g. $HfO_2$).

The enzyme has an active site. The term "active site" refers to the part of the enzyme involved in the interaction with the substrate. It typically comprises a cavity suitable for interacting with the substrate(s). In some case, the active site may comprise several regions such as in the case of a DNA polymerase which comprise a region for ssDNA template (a substrate) entry, a region for nucleotide entry (another substrate), and a region for the output of a newly synthesized dsDNA. Generally, the enzyme comprises a binding pocket for binding with a substrate.

In embodiments, the enzyme may be selected from polymerases, peptidases, and proteases. These enzymes have the advantage that their active site comprise a binding pocket enveloping the substrate to a high degree and thereby expelling the liquid medium present between the substrate and the enzyme body. This makes this kind of enzymes particularly well suited for use with a sensor according to the present disclosure since it removes yet more electrolyte, and hence more screening, from the path between the substrate and the gate dielectric.

In embodiments, the height of the electrolyte-screening layer may be such that more than 10%, more than 20%, more than 30%, usually more than 50% of the height (H, see FIG. 1) of the enzyme is covered. In embodiments, the height of the electrolyte-screening layer may be such that more than 75% or more than 90% of the height of the enzyme is covered. This means that if the enzyme is linked to the dielectric region by a linker (or by a binding layer if no linker is present and the binding layer serves as linker, or by a binding layer and a linker if the linker links the enzyme to a binding layer), the height (h, see FIG. 1) of the electrolyte-screening layer may be equal to the height of the linker (or of a binding layer, or of both a linker and a binding layer) plus more than 10, 20, 30, 50, 75 or 90% of the height of the enzyme. Covering a larger height H of the enzyme can be advantageous because the higher the electrolyte-screening layer, the less the electrolyte can cause screening of the substrate (target molecule). The active site is left uncovered so that the substrate can still interact with the active site. In embodiments, in order to leave the active site uncovered and in order to avoid preventing the target molecule to reach the enzyme, the height of the electrolyte-screening layer may be chosen to be such that less than 100% of the height of the enzyme is covered.

In embodiments, the height of the electrolyte-screening layer may be such that from 2 to 10 nm of the height of the enzyme is covered. Typical heights of oligo ethylene glycol SAMs are 1.2 nm for a trimer, 2.0 nm for a hexamer. These values can help in guiding the person skilled in the art in selecting the length of the molecules forming the electrolyte-screening layer (e.g. in function of the size of the used enzyme).

The electrolyte-screening layer is usually such that the activity of the enzyme is not suppressed. Generally, the electrolyte-screening layer is such that the activity of the enzyme is not reduced. Depending on the enzyme and on the chemical nature of the electrolyte-screening layer, the height of the electrolyte screening layer can be adapted so that the activity of the enzyme is not suppressed. Similarly, the height of the electrolyte screening layer may be adapted so that the activity of the enzyme is not reduced.

To avoid reduction of the enzyme activity as much as possible, the electrolyte-screening layer is usually flexible. For this reason, monolayers (e.g. self-assembled monolayers or monolayers attached to a self-assembled monolayer), lipid monolayers, and lipid bilayers are generally used. Cross-linked layers and layers having a Tg higher than 20° C. may be less advantageous due to their higher rigidity.

The electrolyte-screening layer is typically an organic layer.

The electrolyte-screening layer may work by keeping the electrolyte as far away from the channel as possible. This can be achieved with hydrophilic, hydrophobic or amphiphilic screening layers. In other words, this can be achieved with screening layers comprising hydrophilic, hydrophobic or amphiphilic molecules. The main function of the electrolyte-screening layer would be to physically occupy the place that would otherwise be occupied by the electrolyte.

Although a hydrophobic character provides a better screening than a hydrophilic character, a hydrophilic character permits a better wetting. Better wetting can ease the filling of the fluidic region (which typically comprises a cavity that may measure less than 150 nm, for instance less than 100 nm) and avoids the formation of bubbles on the dielectric region. Such bubbles may be detrimental to the good functioning of the device. For instance, a hydrophilic electrolyte-screening layer, e.g. comprising a polyalkylene glycol such as an oligo or polyethylene glycol (PEG), despite its hydrophilicity, can play a barrier role against the electrolyte and it has the benefit of permitting a better wetting.

In embodiments, the electrolyte-screening layer may double as an anti-fouling layer, i.e. it may prevent non-specific binding of molecules, other than the target, with the dielectric region or the binding layer. For instance, a hydrophilic electrolyte-screening layer, e.g. comprising a polyalkylene glycol such as an oligo or polyethylene glycol (PEG), can play that anti-fouling role.

In embodiments, a hydrophobic layer may be used instead of a hydrophilic layer. The hydrophobic layer may, for instance, comprise molecules having a hydrocarbon chain having zero or more hydrogen atoms substituted by halogen atoms. In embodiments, the halogen atoms are fluorine atoms.

In embodiments, the electrolyte screening layer may be formed of molecules attached to the binding layer. For instance, when the binding layer is a Self-Assembled Monolayer (SAM) with available azide functional groups, the electrolyte-screening layer may be of the formula DBCO-R", wherein DBCO is dibenzocyclooctyne and where R" is an organic chain having a length suitable for covering at least a part of the height of the enzyme, as described above. Examples of organic chains R" are $C_1$-$C_{30}$ organic chains. The organic chain may, for instance, comprise $C_1$-$C_{30}$ alkanes, $C_1$-$C_{30}$ fluoroalkanes, or oligo(ethylene glycol) chains having from 1 to 12 ethylene glycol repeat units. Examples of such a molecule composing a binding layer may have the following formula:

where n is from 1 to 12.

In embodiments, when the electrolyte-screening layer is formed of a self-assembled monolayer of molecules, the density of these molecules on the dielectric region may range from 0.1 to 10 molecules per $nm^2$, from 0.4 to 6 molecules per $nm^2$, or from 1 to 5 molecules per $nm^2$.

In embodiments, an amphiphilic layer is used, the amphiphilic layer having a hydrophobic part and a hydrophilic part, with the hydrophilic part being exposed to the fluidic gate region and hence to the electrolyte when the sensor is in operation. For instance, the electrolyte-screening layer may comprise a lipid monolayer or usually a lipid bilayer such as a cell membrane. In embodiments, a lipid monolayer or bilayer is formed on the dielectric region or on the binding layer. When the electrolyte-screening layer is a lipid monolayer or bilayer, the enzyme is usually a cell membrane enzyme.

Methods for forming such a lipid bilayer on a dielectric region such as a $SiO_2$ region are described in Granéli, Annette, et al. (*Langmuir* (2003), Vol. 19(3), pp. 842-850); C. A. Keller et al. (*Phys. Rev. Lett.*, Vol. 84, pp. 5443); and Reimhult et al. (*Langmuir* (2003), Vol. 19 (5), pp. 1681-1691). Such methods typically involve the use of small unilamellar proteoliposomes mixed with the protein (in our case an enzyme) of interest and a detergent such as Triton X-100 in order integrate the protein into the proteoliposomes, removing the detergent, then contacting the proteoliposomes containing the protein with the dielectric region or the binding layer.

In embodiments, a binding layer may be present on the dielectric region, and the enzyme may be coupled to the dielectric region by being bound to the binding layer.

In embodiments, the electrolyte-screening layer may be bound to the binding layer. In embodiments, both the enzyme and the electrolyte-screening layer may be bound to the binding layer.

In embodiments, the binding layer may be a self-assembled monolayer. The self-assembled monolayer can, for instance, be formed of organosilane molecules. Organosilane molecules can have the advantage of having a functional group (e.g —$SiCl_3$ or —$SiOR'_3$) suitable for attaching covalently to most dielectric material and in particular to oxide materials such as silicon oxide. The organosilane can be chosen so that they possess a functional group permitting attachment to the enzyme (typically via a linker) and/or to the electrolyte-screening layer.

In embodiments, the silane may be of general formula Z—R—X wherein X is a group suitable for attaching to the dielectric region (e.g. X may be $SiOR'_3$ or R—$SiCl_3$)

wherein R is an organic chain (e.g. having from 1 to 20 carbon atoms) and R' is an alkyl (typically methyl or ethyl). Z is a functional group suitable for attaching to the enzyme (e.g. via a linker) and/or to the electrolyte-screening layer. Z is advantageously an azido group or an alkyne group (e.g. a strained alkyne group). When Z is an azido group, the enzyme or more typically the linker attached to the enzyme may have an alkyne group for reacting with the azido group. When Z is an alkyne group, the enzyme or more typically the linker attached to the enzyme may have an azido group for reacting with the azido group.

An example of silane may be an azido-$C_{3-11}$-trimethoxysilane, such as for instance 11-azidoundecyltrimethoxysilane. Such a silane may be deposited as a self-assembled monolayer by vapor phase deposition at 145° C. onto a $SiO_2$ surface.

In embodiments, the binding layer may be an electrografted layer.

In embodiments, the electrografted layer may be formed from molecules having the general formula Z—R—X' wherein R and Z are as defined above and X' is a group suitable for attaching to the dielectric region by electrografting (e.g. X may be a diazonium salt).

In embodiments, the binding layer (e.g. the self-assembled monolayer or the electrografted layer) may be further bound to molecules forming the electrolyte-screening layer on the binding layer. For instance, the binding layer may form an interface layer between on one hand the dielectric region and on another hand the enzyme and the electrolyte-screening layer.

In embodiments, a linker may be attached to the dielectric region or the binding layer, and the enzyme may be coupled to the dielectric region by being bound to the linker.

The linker is typically of formula A-L-E, wherein A is a functional group capable of attaching to the binding layer (e.g. an alkyne such as a strained alkyne group if the binding layer presents an azido group available for reaction, or an azido group if the binding layer presents an alkyne group available for reaction) or to the dielectric region (e.g. an —$SiOR'_3$ or R—$SiCl_3$ group), and E is a functional group capable of attaching to the enzyme, eventually after modification of the enzyme.

Prior to attachment of the linker to the enzyme, the enzyme itself may need to be modified. Examples of E include oxiamine, catechol, alkyne (e.g. a strained alkyne), azide, puromycin, and aniline, amongst others.

Below are a few representative examples of how to attach a linker to an enzyme.

Gilmore et al. (Angew. Chem. Int. Ed. (2006), Vol. 45, pp. 5307-5311) describes a method involving the site-specific modification of the N-terminal position of a protein (which could be replaced by the enzyme of the present disclosure), comprising forming a pyruvamide from the terminal amino group of the protein, followed by reaction with a molecule comprising an oxiamine group (where the molecule could be the linker of the present disclosure and the oxiamine could be the functional group E of the linker).

Song et al. (Acta Biomaterialia (2016), Vol. 43, pp. 50-60) describes a method involving the site-specific modification of the N-terminal position of a protein (which could be replaced by the enzyme of the present disclosure), comprising reacting the protein with a molecule comprising a catechol functional group (where the molecule could be the linker of the present disclosure and the catechol could be the functional group E of the linker).

Temming et al. (Org. Biomol. Chem. (2013), Vol. 11, pp. 2772) describes a method involving the site-specific modification of the N-terminal position of a protein (which could be replaced by the enzyme of the present disclosure), comprising forming a nitrone group from the terminal amino group of the protein, followed by reaction with a molecule comprising a strained alkyne group (where the molecule could be the linker of the present disclosure and the strained alkyne group could be the functional group E of the linker).

Humenik et al. (ChemBioChem (2007), Vol. 8, pp. 1103-1106) describes a method involving the site-specific modification of the C-terminal position of a protein (which could be replaced by the enzyme of the present disclosure), comprising reacting the enzyme with a puromycin linker compring an azide group (where the puromycin linker could be the linker of the present disclosure, the azide group could be the functional group A of the linker).

ElSohly et al. (Acc. Chem. Res. (2015), Vol. 48, pp. 1971-1978) describes the use of oxidative coupling strategies for site-selective protein modification. One described method that could be adapted to the present disclosure and could involve the attachment of an o-azidophenol group at the N-terminal amino acid of the enzyme, followed by reaction with a linker comprising an aniline group, which can photoreact with the o-azidophenol group, and a silane group, which can react with the dielectric region.

Yet other methods that can be similarly adapted to the present disclosure are disclosed in Chen et al. (Chem. Sci. (2017), Vol. 8, pp. 2717), Boutureira et al. (Chem. Rev. (2015), Vol. 115, pp. 2174-2195), Rosen et al. (Nature Chemical Biology (July 2017), Vol. 13, pp. 697-705), Sasaki et al. (Bioorg. Med. Chem. Lett. (2008), Vol. 18, pp. 4550-4553), and Chan et al. (J. Am. Chem. Soc. (2012), Vol. 134, pp. 2589-2598).

The enzyme can be typically bound to the binding layer and/or the linker in such a way that the active site may be accessible from the liquid medium, i.e. the active site is exposed to the fluidic gate.

In embodiments, the part of the enzyme closest to the dielectric region may be within 2 nm, usually within 1 nm of the dielectric region. This means that in embodiments, the enzyme may be separated from the dielectric region by a binding layer and/or a linker whose combined height is 2 nm or less, or 1 nm or less. In embodiments, the part of the enzyme closest to the dielectric region may be in contact therewith. One way to achieve this could be to use an enzyme having a hydrophilic part and a hydrophilic dielectric region. A greater proximity between the target molecule and the channel can translate into a greater sensitivity.

The fluidic gate region may be located above the dielectric region and may be suitable for exposing the active site of the enzyme to the liquid medium. The fluidic gate region typically is or comprises a cavity in a layer of the sensor, said cavity exposing the active site of the enzyme. In embodiments, the lateral extent of the cavity may typically be 150 nm or less, usually 100 nm or less. The sensor typically has a layer above the dielectric region and this layer may have a cavity therein exposing the active site of the enzyme and typically also exposing the entire enzyme and the electrolyte screening layer. In some embodiments, the fluidic gate region may be filled with the liquid medium. The liquid medium can be typically an electrolyte containing the analyte and serving as a liquid gate. In some embodiments, the fluidic gate region may be at least partially empty (of liquid) or not filled with a liquid. In some embodiments, at least part of the fluidic gate region may be filled with air. This would, for instance, be the case when the sensor is not in use and no liquid is in the fluidic gate region. In some embodiments, an inlet and an outlet for the liquid may be provided to the fluidic gate region. For instance, the inlet may be located on one side of the fluidic gate region and the outlet may be located on the opposing side of the fluidic gate region. Typically, the fluidic gate region can be defined at least partially by the dielectric region or any layer thereon, and sidewalls. In some embodiments, a cover may be located above the fluidic gate region and the fluidic gate region may be defined by the cover, the dielectric region or any layer thereon, and sidewalls (e.g. connecting the cover and the dielectric region or any layer thereon). When a cover is present, an inlet and an outlet can be present in the cover.

The sensor of the present disclosure can be used for peptide or protein sequencing.

For this purpose, the enzyme may be a peptidase or a protease.

The enzyme activity may be monitored electronically which allows identifying/fingerprinting the peptide. In a biosensing device where multiple peptidase and/or protease are used, each of said peptidase and/or protease could be suitable for cleaving a different amino acid. Such peptidase and/or protease are known. For instance, endoplasmic reticulum aminopeptidase 1 usually cleaves Leucine, endoplasmic reticulum aminopeptidase 2 usually cleaves arginine, tobacco etch virus nuclear-inclusion-a endopeptidase usually cleaves cysteine.

The sensor of the present disclosure can be used for polynucleotide (e.g. DNA or RNA) sequencing. For this purpose, the enzyme may be a polynucleotide polymerase, such as a DNA polymerase. The building in of the nucleotides by the enzyme may be electronically monitored which allows determining the sequence of the DNA running through the enzyme. For instance, the change of the nucleotides or the configuration change of the enzyme can be detected.

The field effect transistor of the sensor typically comprises a solid gate electrode placed in the fluidic gate region in such a way that it is in electrical contact with the liquid electrolyte gate when this one is present. The field effect transistor typically further comprises a source electrode and a drain electrode in electrical contact with respectively the source region and the drain region of the active region of the FET.

In a second aspect, the present disclosure relates to a biosensing device comprising a sensor according to any embodiments of the first aspect. In embodiments, the biosensing device may comprise a plurality of sensors according to embodiments of the first aspect. In embodiments, a plurality of sensors, each with a different enzyme, may be present in the biosensing device. In such embodiments, the fluidic gate of each of the plurality of sensors may be in fluidic communication with one another. This can be seen as the plurality of sensors sharing a same fluidic gate.

For instance, in an embodiment, a plurality of sensors, each with a different enzyme, may be formed on a single semiconductor substrate.

In embodiments, the biosensing devices may further comprises FETs having a solid gate (e.g. formed of a gate dielectric and a gate electrode).

Any feature of the second aspect can be as correspondingly described in the first aspect.

In a third aspect, the present disclosure relates to a method for manufacturing a sensor. The method comprises forming a field effect transistor (FET). Forming the FET comprises:
providing an active region comprising a source region, a drain region, and a channel region between the source region and the drain region;
providing a dielectric region on the channel region;
coupling an enzyme to the dielectric region, the enzyme having an active site for interacting with a substrate;
coupling an electrolyte-screening layer to the dielectric region so that the electrolyte-screening layer covers at least part of the enzyme while leaving the active site uncovered, thereby permitting interaction of the substrate with the active site; and
forming a fluidic gate region to which the active site of the enzyme is exposed.

In embodiments, forming the FET comprises:
providing an active region comprising a source region, a drain region, and a channel region between the source region and the drain region;
providing a dielectric region on the channel region;
forming a fluidic gate region exposing the dielectric region;
coupling an enzyme to the dielectric region and in the fluidic gate region; the enzyme having an active site for interacting with a substrate, the active site of the enzyme being exposed to the fluidic gate region; and
coupling an electrolyte-screening layer to the dielectric region and in the fluidic gate region, so that the electrolyte-screening layer covers at least part of the enzyme while leaving the active site uncovered, thereby permitting interaction of the substrate with the active site.

In any embodiments of the third aspect, forming a fluidic gate region may comprise:
providing a sacrificial gate electrode on the dielectric region;
providing an overlayer on the sacrificial gate electrode, the source region, and the drain region;
forming a cavity in the overlayer, thereby exposing the sacrificial gate electrode; and
removing the sacrificial gate electrode, thereby forming the fluidic gate region.

The sacrificial gate electrode may be formed of a material that can be etched selectively with respect to the overlayer and the dielectric region. For instance, the sacrificial gate electrode may be made of poly-Si.

The overlayer may be, for instance, an oxide layer such as a $SiO_2$ layer.

Forming the cavity in the overlayer can for instance be performed by an etching process suitable to selectively etch the overlayer with respect to the sacrificial gate electrode. For instance, a plasma etching process can be used.

Removing the sacrificial gate electrode may comprise a wet etch step. For instance, the sacrificial gate electrode may be physically contacted with an etching liquid suitable for selectively etching the sacrificial gate electrode with respect to the overlayer and the dielectric region. In the case of a poly-Si sacrificial gate and of an oxide overlayer and an oxide dielectric region, a tetramethylammonium hydroxide (TMAH) solution can be used to remove the sacrificial gate.

In embodiments, coupling the enzyme and the electrolyte-screening layer to the dielectric region may comprise a preliminary step of forming a binding layer on the dielectric region. The binding layer may be as defined in the first aspect. For instance, the binding layer may suitable for, on one hand, binding to the dielectric region, and on another hand, binding to the enzyme.

A typical example of binding layer may be a self-assembled monolayer of molecules comprising a trimethoxysilane group for binding with the dielectric region and an azide group for binding with the enzyme. Such a binding layer may for instance be deposited in an oven from the vapor phase.

Once the binding layer is formed, the enzyme is usually bound first therewith and then the electrolyte-screening layer is bound therewith.

Binding the enzyme with the binding layer can be generally performed in such a way that only one enzyme is present in the fluidic gate region on the binding layer. To achieve this, Poisson loading can be used as is well known to the person skilled in the art. For instance, Poisson loading may comprise exposing the binding layer with a volume of liquid having from 10 to 50% (typically from 20 to 37%) of chances of comprising a single enzyme. This typically can result in either one or zero enzyme bound to the binding layer. In the case of a biosensing device comprising a plurality of sensors according to the first aspect, Poisson loading may comprise exposing the plurality of sensors to a volume of liquid having an enzyme concentration such that 10 to 50% (typically from 20 to 37%) of the sensors comprise a single enzyme in their fluidic gate region.

The binding of the enzyme on the binding layer can be generally selective. Selectivity can for instance be achieved by using an enzyme having a linker attached therewith, said linker having a group (such as an alkyne group) as defined in the first aspect. When the enzyme comprises a linker comprising an alkyne group or a strained alkyne group, that group can for instance be reacted with azide groups of the binding layer. The reaction can be performed in the conditions of click chemistry, e.g. in presence (for an unstrained alkyne) or absence (for a strained alkyne) of a Cu catalyst.

Binding the electrolyte-screening layer to the binding layer can for instance be achieved by contacting the binding layer with a liquid comprising polyethylene glycol molecules comprising an alkyne or a strained alkyne such as a dibenzocyclo-octyne group. The reaction can be performed in the conditions of click chemistry, e.g. in presence (for an unstrained alkyne) or absence (for a strained alkyne) of a Cu catalyst.

Any feature of the third aspect can be as correspondingly described in the first or second aspect.

Figure 1:
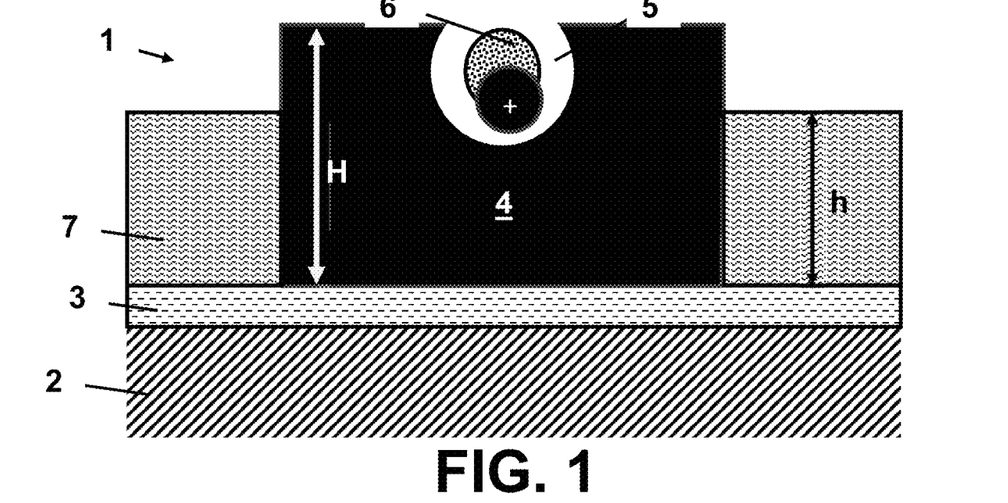
FIG. 1 is a representative schematic illustration of vertical cross-sections of embodiments of the present disclosure and depicts a sensor 1 having an enzyme 4 of height H mounted on a binding layer 3, itself bounded to the dielectric region 2 of the FET. An electrolyte-screening layer 7 of height h is wrapping the mounted enzyme and covers part thereof. An active site 5 is depicted and a substrate 6 having a positive charge is shown inside the active site.
Figure 2:
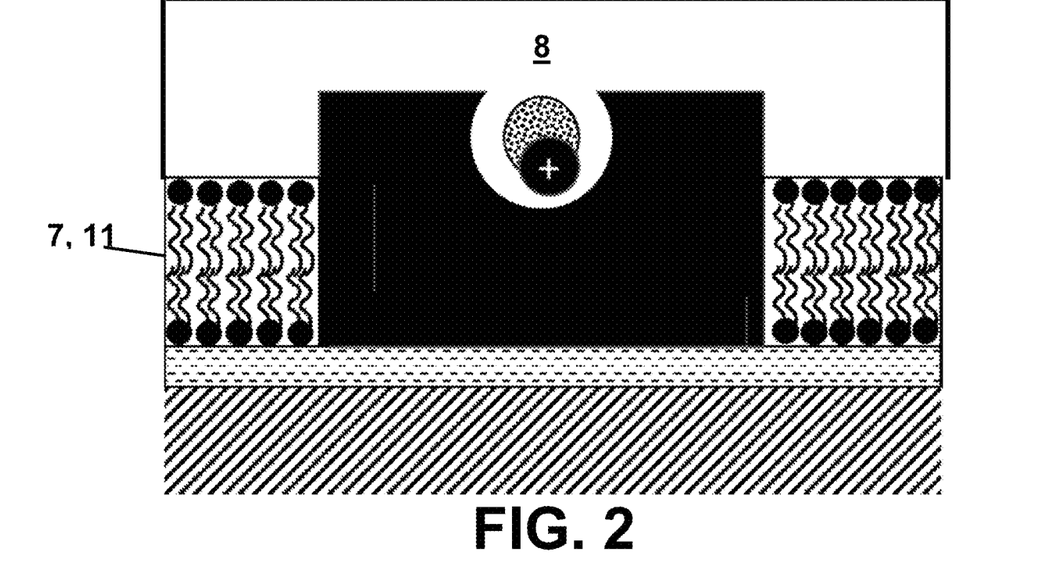
FIG. 2 is a representative schematic illustration of a vertical cross-section of an embodiment of the present disclosure.
Figure 3:
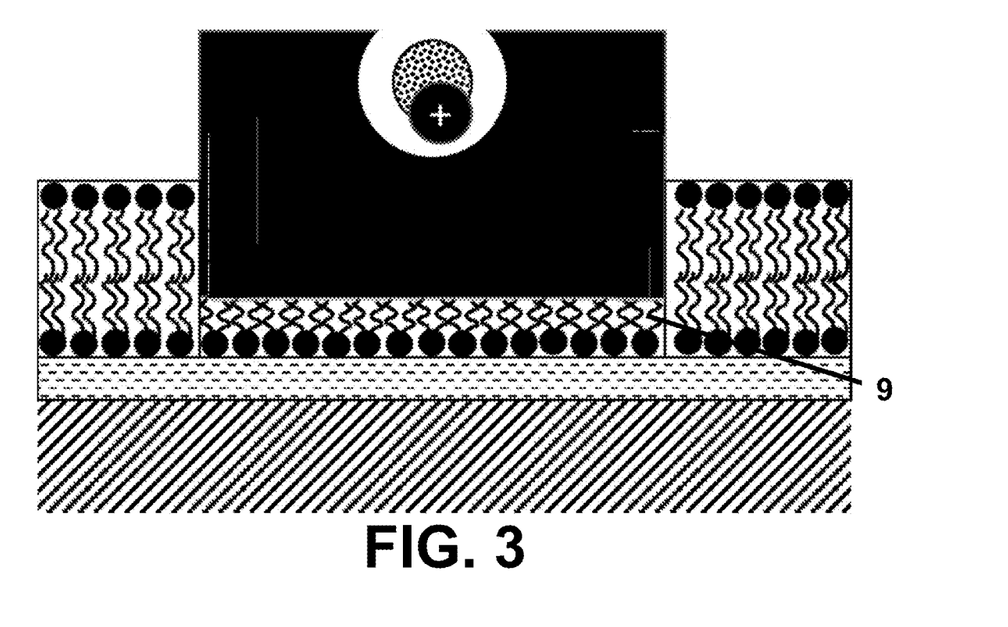
FIG. 3 is a representative schematic illustration of a vertical cross-section of an embodiment of the present disclosure.
Figure 4:
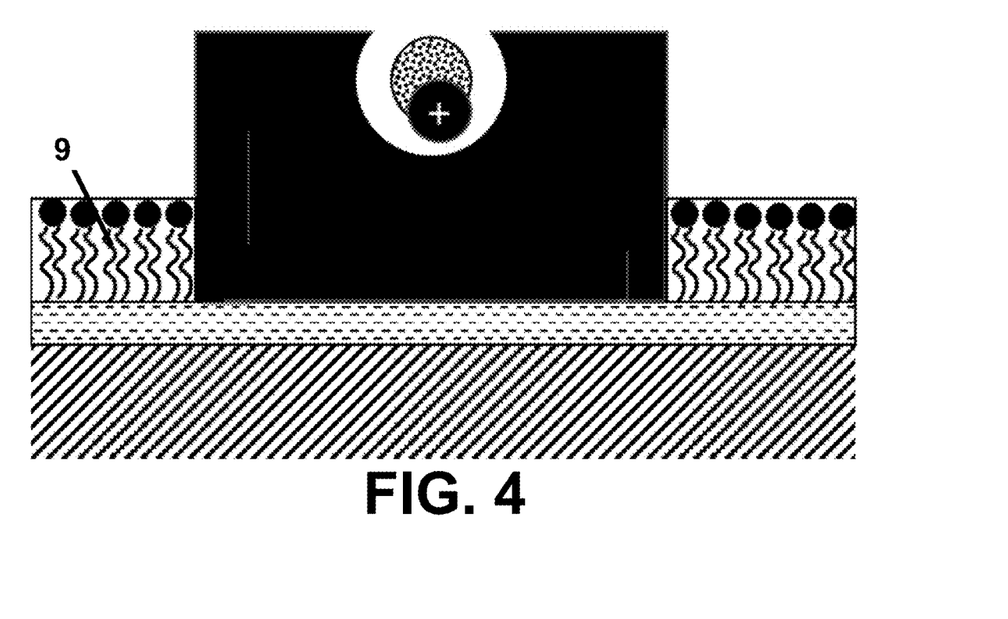
FIG. 4 is a representative schematic illustration of a vertical cross-section of an embodiment of the present disclosure.

FIGS. 1 to 4 are representative schematic illustrations of vertical cross-sections of embodiments of the present disclosure. In FIG. 1, a representative sensor 1 is depicted having an enzyme 4 of height H mounted on a binding layer 3, itself bounded to the dielectric region 2 of the FET. An electrolyte-screening layer 7 of height h is wrapping the mounted enzyme and covers part thereof. An active site 5 is depicted and a substrate 6 having a positive charge is shown inside the active site. FIG. 2 is analogous to FIG. 1 but the electrolyte-screening layer 7 is a lipid bilayer 11. FIG. 2 also depicts the fluidic gate region 8. FIG. 3 is analogous to FIG. 2 but a lipid monolayer 9 is used between the binding layer and the enzyme to provide a good barrier against the electrolyte. FIG. 4 is analogous to FIG. 2, but the lipid bilayer is replaced by a lipid monolayer 9.

Figure 5:
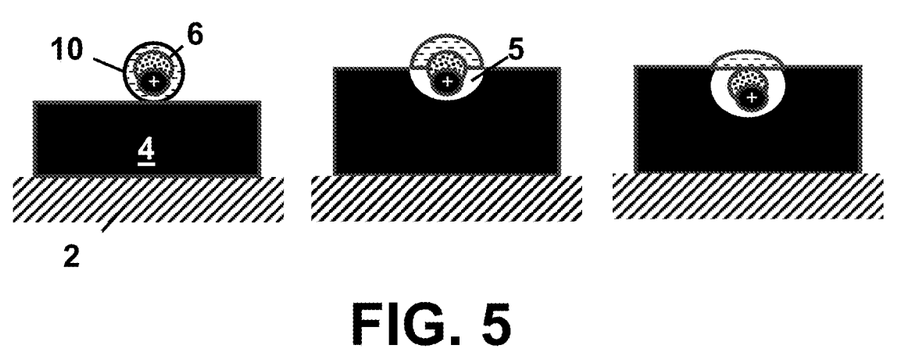

FIG. 5 is a representative schematic illustration of vertical cross-sections of embodiments of the present disclosure. In one less advantageous embodiment shown on the left, a bonded substrate 6 is shown which is not enveloped by the enzyme 4 and hence strongly screened from the channel by the surrounding electrolyte 10. In the two illustrations further to the right, the enzyme is selected in such a way that the active site 5 envelops the substrate to some degree and thereby expels the electrolyte present between the substrate and the enzyme body. The choice of the enzyme and its orientation on the FET dielectric region 2 can be such that screening of the substrate charge by the electrolyte 10 is prevented to a significant extent. Different depths of enveloping binding pockets are illustrated. The envelopment allows reducing screening by the electrolyte.

Figure 6:
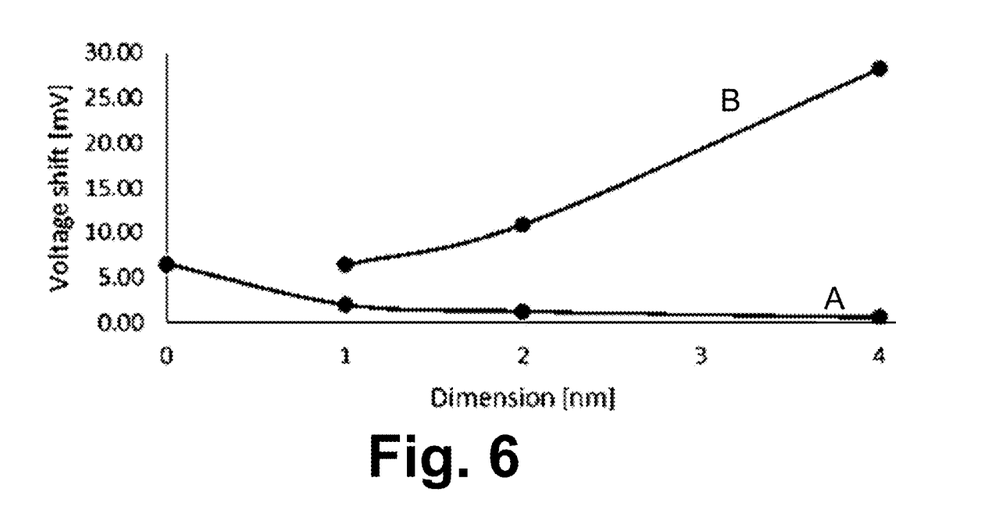
FIG. 6 shows a graph of the voltage shift (mV) observed when an enzyme captures a charged substrate during curve A) simulations of comparative examples and curve B) simulations of embodiments of the present disclosure.

FIG. 6 shows a graph of the voltage shift (mV) observed when an enzyme captures a charged substrate during curve A) Technology Computer Aided Design (TCAD) simulations of comparative examples and curve B) TCAD simulations of embodiments of the present disclosure. The voltage shift is due to three elementary charges. The simulated channel length, width and height were respectively 25 nm, 10 nm, and 10 nm. The presence of a 10× diluted PBS electrolyte was simulated as well.

Figure 7:
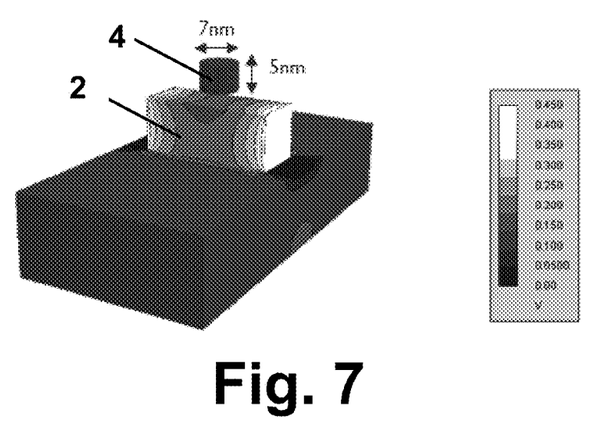
FIG. 7 shows a 3D illustration of a simulated sensor according to an embodiment of the present disclosure.

FIG. 7 is a three-dimensional illustration of the simulated sensor showing the silicon body of the channel 2 and the enzyme 4 modelled as a cylinder. Backfilling is not shown. The calculated voltage is shown in grayscale.

Figure 8:
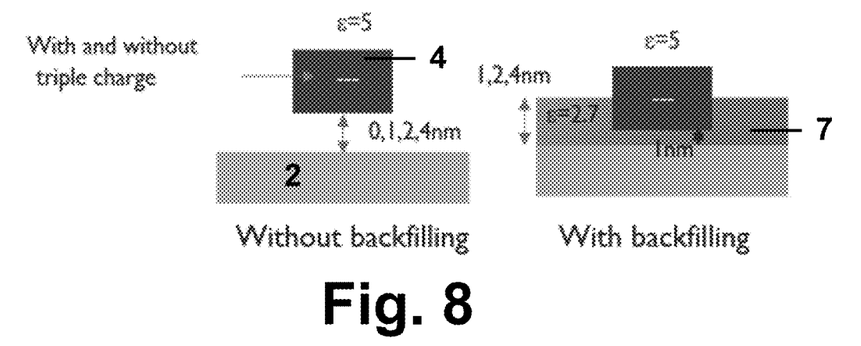
FIG. 8 is a representative schematic illustration of parameters used to simulate a comparative example and an embodiment of the present disclosure.

FIG. 8 is a schematic illustration of the parameters used for the TCAD simulation with and without backfilling.

For the comparative examples, an enzyme was placed in an electrolyte at a distance of 0, 1, 2, 3, or 4 nm of the dielectric region of the sensor. As can be seen in curve A of FIG. 6, the voltage shift quickly decreases with the distance to the dielectric region, in large part due to the presence of electrolyte between the enzyme and the dielectric region.

For the examples according to the present disclosure, an enzyme was kept at a constant distance of 1 nm with respect to the dielectric region but an electrolyte-screening layer was of thickness 1, 2 or 4 nm was used. When the thickness was 1 nm, the space between the enzyme and the dielectric region was filled with the electrolyte-screening layer but the height of the enzyme was not even partially covered. When the thickness was 2 or 4 nm, the height of the enzyme was covered at respectively 20% and 60% respectively. As can be seen in Curve B of FIG. 6, the higher the enzyme height covered, the higher the voltage shift.

It is to be understood that although various embodiments, specific constructions and configurations, as well as materials, have been discussed herein for devices according to the present disclosure, various changes or modifications in form and detail may be made without departing from the scope and spirit of this disclosure. For example, any formulas given above are merely representative of procedures that may be used. Functionality may be added or deleted from the block diagrams and operations may be interchanged among functional blocks. Steps may be added or deleted to methods described within the scope of the present disclosure.

The invention claimed is:

1. A sensor comprising a field effect transistor for sensing a substrate of an enzyme in a sample including electrolyte, the field effect transistor comprising:
    an active region comprising a source region, a drain region, and a channel region between the source region and the drain region;
    a dielectric region on the channel region;
    a binding layer or a linker present on the dielectric region;
    the enzyme coupled to the dielectric region by being bound to the binding layer or the linker, the enzyme having an active site for interacting with the substrate, wherein a portion of the enzyme closest to the dielectric region on the channel region is within 1 nm of the dielectric region;
    an electrolyte-screening layer coupled to the dielectric region and covering part of the enzyme while leaving the active site uncovered, thereby permitting interaction of the substrate with the active site while reducing electrolyte screening by the electrolyte on the substrate; and a fluidic gate region to which the active site of the enzyme is exposed.

2. The sensor according to claim 1, wherein the binding layer is a self-assembled monolayer.

3. The sensor according to claim 2, wherein the self-assembled monolayer is further bound to molecules forming the electrolyte-screening layer on the self-assembled monolayer.

4. The sensor according to claim 3, wherein the molecules are polyalkylene glycol molecules.

5. The sensor according to claim 3, wherein the molecules are selected from hydrocarbon molecules having zero or more hydrogen atoms substituted by halogen atoms.

6. The sensor according to claim 5, wherein the halogen atoms are fluorine atoms.

7. The sensor according to claim 1, wherein the electrolyte-screening layer comprises a lipid bilayer.

8. The sensor according to claim 7, wherein the lipid bilayer is a cell membrane.

9. The sensor according to claim 1, wherein a height (h) of the electrolyte-screening layer is such that from 2 to 10 nm of the enzyme is covered.

10. The sensor according to claim 1, wherein the enzyme is selected from polymerases, peptidases, and proteases.

11. The sensor according to claim 1, wherein the active site of the enzyme comprises a binding pocket for selectively binding the substrate.

12. The sensor according to claim 1, wherein the sensor comprises a single enzyme and is for sensing a single substrate at a time.

13. The sensor according to claim 1, wherein the enzyme is bound to the binding layer via the linker.

14. A biosensing device comprising one or more sensors according to claim 1.

15. The biosensing device according to claim 14, wherein the one or more sensors is a plurality of sensors.

16. The biosensing device according to claim 15, wherein the plurality of sensors are in fluid communication with each other.

17. The biosensing device according to claim 15, wherein each sensor of the plurality of sensors is associated with a different enzyme.

18. The sensor according to claim 1, wherein only a single instance of the enzyme is coupled to the dielectric region on the channel region.

19. The sensor according to claim 1, wherein the enzyme has been modified via site-specific modification of an N-terminal position or a C-terminal position of the enzyme to bind the enzyme to the linker at the N-terminal position or the C-terminal position of the enzyme.

20. The sensor according to claim 1, wherein a positive charge of the substrate, when the substrate is bound to the enzyme within the active site of the enzyme, is located closer to the dielectric region than the height (h) of the electrolyte-screening layer.

* * * * *